United States Patent [19]

Opolski

[11] Patent Number: 5,599,576
[45] Date of Patent: Feb. 4, 1997

[54] MEDICAL APPARATUS WITH SCRATCH-RESISTANT COATING AND METHOD OF MAKING SAME

[75] Inventor: Margaret P. Opolski, Carlisle, Mass.

[73] Assignee: Surface Solutions Laboratories, Inc., Carlisle, Mass.

[21] Appl. No.: 384,422

[22] Filed: Feb. 6, 1995

[51] Int. Cl.⁶ .................................. B05D 1/36; B05D 7/02
[52] U.S. Cl. .............................. 427/2.3; 427/2.24
[58] Field of Search .................... 427/2.1, 2.28, 427/2.29, 2.3, 2.12, 2.24, 2.25

[56] References Cited

U.S. PATENT DOCUMENTS

| | | | |
|---|---|---|---|
| 3,827,115 | 8/1974 | Bom | 29/25.35 |
| 3,937,990 | 2/1976 | Winston | 310/8.3 |
| 4,345,058 | 8/1982 | Dettling | 528/48 |
| 4,427,823 | 1/1984 | Inagaki et al. | 524/833 |
| 4,546,018 | 10/1985 | Ryuzo et al. | 427/408 |
| 4,579,882 | 4/1986 | Kanbe et al. | 523/137 |
| 4,786,453 | 11/1988 | Berger | 264/136 |
| 4,911,718 | 3/1990 | Lee et al. | 623/17 |
| 5,001,008 | 3/1991 | Tokita et al. | 428/400 |
| 5,026,607 | 6/1991 | Kiezulas | 427/2.1 |
| 5,200,263 | 4/1993 | Gould et al. | 428/323 |
| 5,272,012 | 12/1993 | Opolski | 427/2.1 |
| 5,300,558 | 4/1994 | Kurisu et al. | 524/707 |
| 5,338,773 | 8/1994 | Lu et al. | 523/116 |
| 5,407,612 | 4/1995 | Gould et al. | 264/24 |
| 5,474,522 | 12/1995 | Scholz et al. | 602/8 |

FOREIGN PATENT DOCUMENTS

| | | |
|---|---|---|
| 0480809A3 | 4/1992 | European Pat. Off. . |
| WO93/15781 | 8/1993 | WIPO . |

OTHER PUBLICATIONS

JP 60037416, Patent Abstracts of Japan, Feb. 1985, abstract only.

*Primary Examiner*—Diana Dudash
*Attorney, Agent, or Firm*—Choate, Hall & Stewart

[57] ABSTRACT

A method for providing a medical apparatus with a protective surface coating is described. The method comprises applying to a medical apparatus a coating solution that contains a matrix polymer such as a urethane, and a reinforcing agent such as lamellar platelet and fiber additives, as micaceous pigments, flake pigments, tungsten powder and glass fiber, to increase the resistance of the medical apparatus to injury, such that the surface coating forms a protective, scratch- and puncture-resistant layer on the medical apparatus. The particles or fibers of the reinforcing agent may be oriented to provide the medical apparatus with additional resistance to injury. The coating is well suited to provide balloon catheters, particularly PET balloons, and the like with the toughness desirable for use in stent delivery and placement.

19 Claims, No Drawings

MEDICAL APPARATUS WITH SCRATCH-RESISTANT COATING AND METHOD OF MAKING SAME

BACKGROUND OF THE INVENTION

As medical science delves into smaller areas of the body, such as blood vessels, it has become increasingly difficult to reach these areas with an effective conventional apparatus. In part, this is due to the materials from which the apparatus is made, and the dangers to the apparatus due to the methods of introduction into the body and in particular, the small areas of the body. Particularly, catheters having inflatable balloon attachments have been used for reaching these small and related areas, such as in coronary angioplasty. More particularly, stent delivery and placement devices useful for opening occluded or blocked vessels have been used in coronary and peripheral angioplasty, urology and reproductive surgeries, among others.

Balloon catheters are produced from materials that can sustain large amounts of pressure. However, the profile of balloon catheters and related devices must be small in order to be introduced into the small areas of the bodies, such as blood vessels. Therefore, materials with high strength relative to film thickness are chosen. An example of these materials is PET (poly-ethylene terephthalate), which is useful for providing a non-compliant, high-pressure device for delivering a stent to a vessel. Unfortunately, PET and other materials with high strength to film thickness ratios tend to be scratch and puncture sensitive. Polymers that tend to be less sensitive to scratches, such as polyethylene, nylon, and urethane are compliant, and at the same film thickness as the non-compliant PET, do not provide the strength required to withstand the pressure used for delivering a stent into a vessel wall. Non-compliance, or the ability not to expand beyond a predetermined size on pressure and to maintain substantially a profile, is a desired characteristic for balloon catheters, particularly for use in small vessels, so as not to rupture or dissect the vessel as the balloon expands. A layer added on the substrate may provide some protective characteristics to a medical apparatus by virtue of the added thickness, and many resins may be used for this purpose. However, such a physical barrier, provides only limited protection.

Further difficulties often arise in guiding a catheter into a desired location in a patient due to the friction between the apparatus and the vessel through which the apparatus passes. The result of this friction is failure of the balloon due to abrasion and puncture during handling and use and also from over-inflation. There has been attention in the field to providing lubricious coatings to the medical apparatus to diminish friction that causes apparatus failure. One such lubricious coating for balloon catheters is described in U.S. Pat. No. 5,272,012 to Opolski, wherein the use of a slip additive such as a siloxane is disclosed. These coatings improve the success rates of balloon catheters by altering the friction coefficient by use of lubricious coatings. However, they do not address the scratch and puncture-resistance of the apparatus other than by building film thickness, which is inadequate protection against destruction of the balloon by tears, scratches, punctures and the like, particularly for the delivery of stenting devices.

SUMMARY OF THE INVENTION

The present invention relates to a medical apparatus having and a method for providing a medical apparatus with a protective surface coating containing a matrix polymer and a reinforcing agent to decrease the sensitivity of the medical apparatus to injuries, such as scratches, punctures, and the like. The reinforcing agent may be oriented in the coating to provide enhanced injury resistance. The surface coating forms a protective layer on the medical apparatus to provide resistance to scratches, punctures and the like, and is well suited to an apparatus that is required to withstand pressure and maintain a small profile.

DETAILED DESCRIPTION OF THE INVENTION

As used herein, the term "medical apparatus" means apparatus suited for use in medical applications, particularly in in vivo applications. Such apparatus specifically includes, but is not limited to, balloons, catheters, guidewires, stylets and introducers. Of particular note for use with the invention are catheters having inflatable balloons such as those developed for use in angioplasty and valvuloplasty, urology, gynecology, neurology and the like.

As used herein, the term "reinforcing agent" means a substance capable, when in a coating, of increasing the hardness of the surface of a medical apparatus and allowing a fracture plane within the coating without loss of coating from the substrate. Preferably, the reinforcing agent has a higher surface hardness than the surface hardness of the medical apparatus. Preferred reinforcing agents include lamellar platelet and fiber additives, such as micaceous pigments, flake pigments, and glass. Glass fibers may be obtained pretreated with silane, such as 737BC, available from Owens-Corning, Toledo, Ohio.

As used herein, the term "matrix polymer" means a polymer capable of forming a coating on the surface of a medical apparatus and providing a network for containing a reinforcing agent such as a solvent, water, UV curing or 100% solids polymer. The matrix polymer preferably has functional moieties capable of crosslinking to other moieties within the matrix polymer and with moieties derived from the medical apparatus to enhance the strength, adhesion and toughness of the coating. Examples of matrix polymers include resin systems such as urethane, acrylics, and epoxies or others selected for non-substrate attack and curing temperature properties. Water-based urethanes are particularly desirable due to their protective qualities allowing crosslinking within the urethane itself and binding with carboxyl groups present on the surface of the medical apparatus or derived at the surface with pretreatments or primers.

The language "moieties derived from the medical apparatus" is intended to include functional moieties from the material of which the medical apparatus is made, moieties from a primer layer disposed between the coating and the medical apparatus or moieties generated or formed by subjecting the primer layer to a pretreatment step, e.g., plasma or corona discharge.

In the case of most water-based coatings, e.g. urethane based, bonding of the coating to the substrate surface upon which it is applied can be achieved by use of an optional crosslinking agent, such that there is reaction between carboxyl functional groups present in the coating, e.g., urethane, and carboxyl functional groups present on the substrate surface. One method by which such bonding can be achieved involves a crosslinking reaction using polyfunctional aziridine through which the linkage will occur. Crosslinking agents are added optionally to provide improved hardness, adhesion and chemical and water resistance.

As used herein, the term "crosslinking agent" is intended to include agents capable of enhancing the molecular weight of the matrix polymer. The crosslinking agent further may enhance the adhesion of the coating to the medical apparatus. For example, functional moieties of the matrix polymer may be crosslinked to the function moieties derived from the medical apparatus. The functional moieties are intended to include groups capable of binding to one another. The matrix polymer may be selected for such functional moieties. Examples of crosslinking agents useful within this invention are aziridine, carbodiimides, urea formaldehyde and melamine formaldehyde condensates, epoxies, isocyanates, titanates, zircoaluminates, zinc crosslinkers, and silanes. One skilled in the art would be able to select the crosslinking agent based upon the functional moieties desired to be crosslinked and the substrate temperature limitations.

As used herein, the term "primer layer" is intended to include a layer capable of providing the desired adhesion to substrate and/or functional moieties for crosslinking to the matrix polymer or reinforcing agent. The primer layer is disposed between the medical apparatus and the matrix polymer. A material that is useful and desirable for making medical apparatus may not possess adhesion or functional moieties capable of crosslinking sufficiently with a desired matrix polymer or reinforcing agent. In this situation, the desired adhesion or functional moieties can be provided to the surface of the medial apparatus by coating the apparatus with a primer layer. An example of such a layer is a dispersion of ethylene acrylic acid (EAA), such as Primacor 5980 available from Dow-Corning Corporation (Midland, Mich.), or MICHEMPRIME 4983R available from Michelman (Cincinatti, Ohio), or which is capable of providing carboxyl moieties to the surface.

As an alternative to the use of a primer, a surface functionality can be obtained on the substrate surface using a number of other techniques. For example, surface functionality can be obtained using a plasma or corona discharge or by exposing the surface to a flame. In the case of plasma or corona discharge, the functionality obtained on the surface can be tailored through the use of process atmosphere variation. Thus when an oxygen-derived functionality (i.e. —OH or —COOH) is desired, the surface can be plasma treated in an oxygen-containing atmosphere. Alternatively, if an amine functionality is preferred, the treating process can be carried out in a nitrogen containing atmosphere.

As used herein the term "coating solution" is intended to include a solution containing both the matrix polymer and the reinforcing agent capable of being coated on a surface of a medical apparatus. The coating solution also may include other materials that do not detrimentally effect the protective compound and reinforcing agent network. These materials include radiopacifiers, anti-slip additives, anti-mar additives, therapeutic agents, and antimicrobial agents. The term therapeutic agent for purposes of this invention is intended to include substances capable of providing a therapeutic effect in the environment of use of the medical apparatus. The therapeutic agents may be anti-inflammatory agents, antibiotics, immune-suppressible stimulatory agents, anti-thrombolytic agents, growth factors, agents that locally effect blood pressure, agents that promote cell survival and healing, and the like. Antimicrobial agents are agents capable of suppressing the growth or activity of microorganism allowing them to combat infections. Examples of classes of antimicrobial agents include antibiotics, iodine solutions, mercurials nitroimidazoles, bisguanidessilier, phenolics, ammonium salts, silver compounds and the like. Specific examples of agents within classes include metronidazole and chlorhexidine. One of ordinary skill in the art would be able to select agents capable of attaining a desired function or result.

The surface of the apparatus may be prepared for application of the coating solution by pretreatment as needed for adhesion. Such preparation includes corona, plasma, flame and primer pretreatments.

The coating can be applied to a substrate using any of a variety of methods. Preferred among these are dipping, spraying, flowing, rolling and brushing. Orienting the particles or fibers of the reinforcing agent in the coating solution as it is applied to the medical apparatus is desired. Orientation of the particles or fibers of the reinforcing agent so as to be aligned in a direction perpendicular to the direction of likely injury, and may be accomplished by application shear, including dip pull-out, direction rotation through solution, flow and spin orientation, surface tension and evaporative effects. A low solids coating may be dipped more than once and may be most uniform for thickness, especially if oriented to allow sag to one end on one dip, and to a different orientation on a second dip. Possibilities exist for orienting by rotating through the coating on the axis of the apparatus and then drying in this configuration. Agitation may be needed during application to maintain adequate consistency and inhibit skinning at the surfaces. Such agitation will be required in accordance with manufacturer's instructions in connection with the raw materials used, and may be based on the stability to shear of the reinforcing agent.

Film thickness of the coating is preferably in the range of about 0.1 to about 3 mils, and most preferred in the range of about 0.5 to about 2 mils. Adjustments to the viscosity and solids of the coating solution will accomplish the desired thickness and will be apparent to one of ordinary skill in the art. In the embodiment containing micaceous pigment as the reinforcing agent, the micaceous pigment concentration should be increased with decreasing thickness of film to allow increased scratch and puncture resistance. The concentration of the reinforcing agent may be in the range of from about 1% to about 95% by weight of solids. The preferred concentration of reinforcing agent is in the range of about 10% to about 50% by weight of solids. However, too great a concentration may degrade polymer properties and begin to affect performance.

The curing may be carried out by first holding the coated apparatus at ambient temperature to allow equilibration and foam to break. Air drying is possible for ambient cure systems, and can be accelerated by heat cure at elevated temperature. Certain crosslinking agents may need a certain time at an elevated temperature to allow cure and this may be accomplished by placing the coated apparatus in an oven, e.g. at approximately 50° C. for a PET substrate, until the matrix polymer is fully dried. The temperature selected for the curing step may depend on the temperature limitations of the substrate and the reactivity of the crosslinking agent.

The resulting coating provides resistance to scratches, punctures and the like, thereby decreasing the sensitivity of the medical apparatus to injury. This decreased sensitivity is the result of the matrix polymer and the reinforcing agent in the coating solution. The coating solution containing a matrix polymer and a reinforcing agent provides the coating of the present invention with resistance to scratches, punctures and the like that is enhanced over that which is provided by the matrix polymer alone. A reinforcing agent with a surface hardness that is higher than that of the surface hardness of the apparatus is preferred. Orientation of the fibers of the reinforcing agent so as to be aligned in a direction perpendicular to the direction of insertion into the body and small areas of the body is preferred. Micaceous or flake pigments used as the reinforcing agent may be oriented parallel to the surface of the device.

EXAMPLE 1

A coating solution prepared in accordance with the teachings of this invention and having the following formulation is provided:

| Component | Supplier/Designation | Weight (%) |
|---|---|---|
| Urethane | R9621/Zeneca Resins | 82.2 |
| Micaceous pigment | 110 Silver Pearl/ EM Industries | 6.5 |
| Crosslinking Agent | CX100/Zeneca Resins | 3.7 |
| Acetone | — | 3.7 |
| Water | — | 3.7 |

The coating solution is prepared by prewetting and dispersing the micaceous pigment (3.5 g) (110 Silver Pearl obtained from EM Industries, Hawthorne, N.Y.) into a solution of distilled water (2 g) and acetone (2 g) to reduce the tendency to foam. The urethane dispersion (44 g) (R9621 obtained from Zeneca Resins, Wilmington, Mass.) was added with agitation provided by a magnetic stirrer. Finally, the crosslinking agent (2 g) (CX100 obtained from Zeneca Resins) was added dropwise and allowed to stir for 30 minutes prior to application.

A PET balloon had been plasma treated (300 W, 0.25 Torr oxygen for 5 minutes) and dipped into a 15% solids emulsion of primer (MICHEMPRIME 4983R obtained from Michelman, Cincinatti, Ohio), and the then dried for 5 minutes at 46° C. before the coating solution was applied. The coating solution was applied by dip, then cured and dried for 1 hour at 46° C.

EXAMPLE 2

A coating solution prepared in accordance with the teachings of this invention and having the following formulation is provided:

| Component | Supplier/Designation | Weight (%) |
|---|---|---|
| Urethane | R972 (Zeneca Resins) | 50 |
| Glass fiber | 737BC (Owens-Corning) | 5.1 |
| Crosslinking agent | CX100/Zeneca Resins | 2 |
| Water | — | 42.9 |

The urethane dispersion, glass fiber (737BC obtained from Owens-Corning, Toledo, Ohio) and water were mixed with agitation provided by a magnetic stirrer. The crosslinking agent was added dropwise and allowed to stir for 30 minutes prior to application.

The coating solution was applied to a PET balloon that had been corona treated achieved by rotating the balloon for 1 minute within ½" of corona generated by a Model BD-20 with a 3" electrode, BD-20 supplied by Electro-Technics, Chicago, Ill.) and dipped into a 15% solids emulsion of primer (Primacor 5980, Dow Chemical, Midland, Mich.), and dried for 5 minutes at 46° C. The coating solution was applied by flow coating, then cured and dried for 1 hour at 46° C.

EXAMPLE 3

A coating solution prepared in accordance with the teachings of this invention and having the following formulation is provided:

| Component | Supplier/Designation | Weight (%) |
|---|---|---|
| Urethane | R9621/Zeneca Resins | 6.8 |
| Water | | 67.9 |
| Tungsten Powder | M10/GTE Osram | 23.2 |
| Thickening Agent | ASE-60 Acrysol/Rohm & Haas | 2.0 |

The coating solution was prepared by combining the urethane and water. The thickener may be added dropwise with agitation and the solution pH adjusted to 9 with ammonium hydroxide to allow the viscosity to increase. The tungsten powder was added and stirred into the thickened solution.

A PET balloon prepared with a corona treatment (as in Example 2) and primer dipped (MICHEMPRIME 4983 as in Example 1) was flow coated with the tungsten reinforced coating solution and dried for 1 hour at 46° C.

Coated and uncoated balloons were scratch tested with the results that the testing of uncoated balloons resulted in complete destruction of the balloon, whereas the coated balloons resisted the injury, resulting in only discrete damage to the effected area.

I claim:

1. A method for providing a protective coating on a surface of a medical apparatus adapted for use within a patient, comprising:

applying a coating solution to a surface of an implantable medical apparatus, such that a protective layer is formed upon the apparatus surface, wherein the coating solution comprises a matrix polymer which contains a reinforcing agent, the reinforcing agent having a higher surface hardness than the surface hardness of the medical apparatus, wherein a total coating thickness on the medical apparatus is no greater than about 3 mil (0.003 inch).

2. A method for providing a protective coating on the surface of a medical apparatus in accordance with claim 1, wherein said protective layer has a thickness in the range of about 0.1 mil to about 3 mil.

3. A method for providing a providing a protective coating on a surface of a medical apparatus in accordance with claim 1, wherein the matrix polymer is urethane.

4. A method for providing a protective coating on a surface of a medical apparatus in accordance with claim 1, wherein the matrix polymer is epoxy.

5. A method for providing a providing a protective coating on a surface of a medical apparatus in accordance with claim 1, wherein the reinforcing agent of the coating solution comprises a lamellar material.

6. A method for providing a providing a protective coating on a surface of a medical apparatus in accordance with claim 5, wherein the lamellar reinforcing agent of the coating solution comprises a micaceous pigment.

7. A method for providing a providing a protective coating on a surface of a medical apparatus in accordance with claim 1, wherein the reinforcing agent of the coating solution comprises a fiber.

8. A method for providing a providing a protective coating on a surface of a medical apparatus in accordance with claim 7, wherein the fiber reinforcing agent of the coating solution comprises glass.

9. A method for providing a providing a protective coating on a surface of a medical apparatus in accordance with claim 1, wherein the reinforcing agent is selected from the group consisting of lamellar platelets, flake pigments and fibers.

10. A method for providing a protective coating on a surface of a medical apparatus in accordance with claim 1, further comprising applying a primer to the surface of the medical apparatus.

11. A method for providing a providing a protective coating on a surface of a medical apparatus in accordance with claim 1, wherein the coating solution further comprises a crosslinking agent.

12. A method for providing a protective coating on a medical apparatus in accordance with claim 11, wherein the crosslinking agent is aziridine.

13. A method for providing a protective coating on a surface of a medical apparatus in accordance with claim 1, wherein the medical apparatus comprises a catheter.

14. A method for providing a protective coating on a surface of a medical apparatus in accordance with claim 1, wherein the medical apparatus comprises a balloon.

15. A method for providing a protective coating on the surface of a medical apparatus in accordance with claim 1, wherein said protective layer has a thickness in the range of about 0.2 mil to about 2 mil.

16. A method for providing a protective coating on the surface of a medical apparatus in accordance with claim 1, wherein the step of applying a coating solution to the apparatus surface is performed two or more times.

17. A method for providing a protective coating on the surface of an implantable medical apparatus adapted for use within a patient, comprising:

applying a coating solution to a surface of the medical apparatus, the coating solution comprising a reinforcing agent, the reinforcing agent containing fibers, such that a protective coating is formed on the apparatus surface; and aligning the fibers on the surface of the medical apparatus in a direction parallel to the apparatus surface.

18. A method for providing a protective coating on the surface of an implantable medical apparatus adapted for use within a patient, comprising:

applying a coating solution to a surface of the medical apparatus, such that a protective layer is formed upon the apparatus surface, such that a total coating thickness on the medical apparatus is no greater than about 3 mil, wherein the coating solution comprises a matrix polymer which contains a reinforcing agent, the reinforcing agent containing particles having a higher surface hardness than the surface hardness of the medical apparatus; and aligning the particles on the surface of the medical apparatus in a direction parallel to the apparatus surface.

19. A method for providing a protective coating on the surface of a medical apparatus in accordance with any one of claims 1, 17 and 18, wherein said implantable medical apparatus is temporarily implantable.

* * * * *

UNITED STATES PATENT AND TRADEMARK OFFICE
CERTIFICATE OF CORRECTION

PATENT NO. : 5,599,576

DATED : February 4, 1997

INVENTOR(S) : Margaret P. Opolski

It is certified that error appears in the above-identified patent and that said Letters Patent is hereby corrected as shown below:

In column 3, line 27; before "apparatus", please delete "medial" and insert therefore --medical--.

In column 5, line 35; after "and", please delete "the".

In claim 3, line 1; after "providing", please delete "a providing".

In claim 5, line 1; after "providing", please delete "a providing".

In claim 6, line 1; after "providing", please delete "a providing".

In claim 7, line 1; after "providing", please delete "a providing".

UNITED STATES PATENT AND TRADEMARK OFFICE
CERTIFICATE OF CORRECTION

PATENT NO. : 5,599,576
DATED : February 4, 1997
INVENTOR(S) : Margaret P. Opolski It is certified that error appears in the above-identified patent and that said Letters Patent is hereby corrected as shown below:

In claim 8, line 1; after "providing", please delete "a providing".

In claim 9, line 1; after "providing", please delete "a providing".

In claim 11, line 1; after "providing", please delete "a providing".

In claim 17, line 1; after "on", please delete "the" and insert therefor --a--.

In claim 18, line 1; after "on", please delete "the" and insert therefor --a--.

Signed and Sealed this

Eighth Day of December, 1998

*Attest:*

BRUCE LEHMAN

*Attesting Officer*  Commissioner of Patents and Trademarks